United States Patent
Williamson et al.

[19]

[11] Patent Number: 5,925,077
[45] Date of Patent: Jul. 20, 1999

[54] APPARATUS AND METHOD FOR PLUGGING HOLES IN AN ACETABULAR SHELL COMPONENT

[75] Inventors: Daniel E. Williamson, Warsaw, Ind.; Jane Sheetz, Round Rock, Tex.; Richard Craig Blaschke, South Glamorgan, United Kingdom

[73] Assignee: Biomet, Inc., Warsaw, Ind.

[21] Appl. No.: 08/832,477

[22] Filed: Apr. 2, 1997

[51] Int. Cl.⁶ ........................................................ A61F 2/32
[52] U.S. Cl. ................................................................ 623/22
[58] Field of Search ........................ 623/22, 23; 606/65, 606/66, 72, 73, 86, 89, 104

[56] References Cited

U.S. PATENT DOCUMENTS

| | | | |
|---|---|---|---|
| 3,840,904 | 10/1974 | Tronzo | 3/1 |
| 3,866,248 | 2/1975 | Kummer | 3/1 |
| 3,906,550 | 9/1975 | Rostoker et al. | 3/1.912 |
| 4,001,928 | 1/1977 | Schweiso | 29/447 |
| 4,285,071 | 8/1981 | Nelson et al. | 3/1.912 |
| 4,417,571 | 11/1983 | Nelson et al. | 128/92 |
| 4,563,778 | 1/1986 | Roche et al. | 623/22 |
| 4,566,138 | 1/1986 | Lewis et al. | 623/22 |
| 4,659,331 | 4/1987 | Matthews et al. | 623/20 |
| 4,666,450 | 5/1987 | Kenna | 623/22 |
| 4,711,234 | 12/1987 | Vives et al. | 128/92 |
| 4,778,473 | 10/1988 | Matthews et al. | 623/20 |
| 4,883,491 | 11/1989 | Mallory et al. | 623/22 |
| 4,919,666 | 4/1990 | Buchhorn et al. | 623/16 |
| 4,923,473 | 5/1990 | Griss et al. | 623/22 |
| 4,936,856 | 6/1990 | Keller | 623/22 |
| 4,944,759 | 7/1990 | Mallory et al. | 623/22 |
| 4,955,325 | 9/1990 | Zarnowski et al. | 623/22 |
| 4,955,917 | 9/1990 | Karpf | 623/22 |

(List continued on next page.)

| | | |
|---|---|---|
| 5,725,580 | 3/1998 | Cloutier et al. . |

FOREIGN PATENT DOCUMENTS

| | | |
|---|---|---|
| 0 346 270 A1 | 1/1989 | European Pat. Off. . |
| 2 638 963 A1 | 11/1988 | France . |
| 2 685 192 A1 | 12/1991 | France . |
| WO 95/30389 | 11/1995 | WIPO . |
| WO 96/03096 | 2/1996 | WIPO . |
| WO 96/23457 | 8/1996 | WIPO . |

OTHER PUBLICATIONS

Intermedics Orthopedics, Inc., Inter–Op Acetabular System; Copyright 1997 (4 pp.).
Biomet, Inc., Vision Hip System Acetabular Series, copyright 1996 (19 pp.).

*Primary Examiner*—Mickey Yu
*Assistant Examiner*—John M. Black
*Attorney, Agent, or Firm*—Harness, Dickey & Pierce, P.L.C.

[57] ABSTRACT

This invention relates to an apparatus and method for plugging holes in an acetabular shell component. The apparatus includes an acetabular shell component having an inner concave surface and an outer convex surface with at least a first selectively pluggable hole passing therethrough. The first selectively pluggable hole being defined by at least a cylindrical threaded sidewall. The apparatus further includes a plug having a tapered threaded sidewall. The cylindrical threaded sidewall of the first selectively pluggable hole threadably receives the tapered threaded sidewall of the plug to create an interference fit. This interference fit substantially seals the first selectively pluggable hole to minimize migration of debris through the first selectively pluggable hole. The apparatus further includes a second selectively pluggable hole and a removal instrument which is operable to removably engage a second plug without scratching the inner concave surface of the acetabular shell component during the removal of the second plug.

11 Claims, 6 Drawing Sheets

U.S. PATENT DOCUMENTS

| | | | |
|---|---|---|---|
| 5,009,665 | 4/1991 | Serbousek et al. | 623/22 |
| 5,021,062 | 6/1991 | Adrey et al. | 623/22 |
| 5,032,134 | 7/1991 | Lindwer | 623/22 |
| 5,041,141 | 8/1991 | Ypma et al. | 623/23 |
| 5,156,625 | 10/1992 | Marchetti et al. | 623/22 |
| 5,197,989 | 3/1993 | Hinckfuss et al. | 623/23 |
| 5,211,665 | 5/1993 | Ku | 623/22 |
| 5,217,499 | 6/1993 | Shelley | 623/22 |
| 5,226,917 | 7/1993 | Schryver | 623/22 |
| 5,282,864 | 2/1994 | Noiles et al. | 623/18 |
| 5,310,408 | 5/1994 | Schryver et al. | 623/22 |
| 5,314,487 | 5/1994 | Schryver et al. | 623/22 |
| 5,314,494 | 5/1994 | Huiskes et al. | 623/23 |
| 5,360,452 | 11/1994 | Engelhardt et al. | 623/22 |
| 5,370,702 | 12/1994 | Jones | 623/22 |
| 5,387,242 | 2/1995 | Miser | 623/22 |
| 5,549,694 | 8/1996 | Noiles et al. | 623/22 |
| 5,571,198 | 11/1996 | Drucker et al. | 623/22 |

APPARATUS AND METHOD FOR PLUGGING HOLES IN AN ACETABULAR SHELL COMPONENT

BACKGROUND OF THE INVENTION

1. Field of the Invention

This invention relates generally to an apparatus and method for use in orthopedic surgery and, more particularly, to an apparatus and method for plugging holes in an acetabular shell component and the associated instruments used for inserting and removing plugs in the acetabular shell component.

2. Discussion of the Related Art

A natural hip joint may undergo degenerative changes due to a variety of etiologies. When these degenerative changes become so far advanced and irreversible, it may ultimately become necessary to replace a natural hip joint with a prosthetic hip. When implantation of such a hip joint prosthesis becomes necessary, the head of the natural femur is first resected and a cavity is created within the intramedullary canal of the host femur for accepting the hip prosthesis. The hip prosthesis may be inserted and supported within the host femur by cementing the hip prosthesis within the host femur or by using an impact method where the hip prosthesis is snugly fit within and is supported by the host femur. If the acetabulum also needs repair, all remnants of articular cartilage are generally removed from the acetabulum and an acetabular prosthesis which will accommodate the head or ball of the hip prosthesis is affixed to the acetabulum. The acetabular prosthesis is affixed to the acetabulum by means of cement, screws or other appropriate fixation means.

An impact type acetabular prosthesis which is stabilized by means of fixation screws generally includes an acetabular shell component and a polymeric shell liner. The acetabular shell component includes a smooth inner concave surface, a roughened outer convex surface and a plurality of holes passing therethrough for receipt of the fixation screws. The fixation screws may be installed into all of the holes or only some of the holes depending on the patient's requirements. The polymeric shell liner seats against the smooth inner concave surface and acts as a bearing surface for the head of the hip prosthesis. As the hip prosthesis is loaded, micromotion may occur between the acetabular shell component and the polymeric shell liner, potentially resulting in wear debris being formed between the shell component and the shell liner. Since some of the holes in the shell component may not receive fixation screws, the wear debris may pass through these open holes and out of the shell component.

To seal or cover the holes, some acetabular prostheses utilize plugs to cover the holes formed in the acetabular shell component. For example, U.S. Pat. No. 5,310,408 provides for a closure member which may be pressed into selected openings after implantation of the shell component or removed before implantation of the shell component. U.S. Pat. No. 4,955,325 provides for cement spacers which lock into apertures in the shell to provide for a cement mantel. U.S. Pat. No. 4,955,325 also provides for a threaded plug which is utilized for closing a complimentary threaded center hole in the shell component. However, use of the above-identified plug mechanisms suffer from many disadvantages.

Specifically, in U.S. Pat. No. 5,310,408, the closure members, if inserted into the shell component during manufacture, must be removed before the shell component is implanted, should it be desirable to use the selected holes (i.e. remove by applying pressure on the outer concave side). This procedure reduces the surgical flexibility by requiring a surgeon to determine which closure members should be removed prior to actually implanting the shell component. Moreover, no mechanism for removal of the closure members is taught. Still further, should it be required for the surgeon to plug the various holes with the closure members once the shell component has been implanted into the patient, this increases the surgical time and cost.

In U.S. Pat. No. 4,955,325, the complimentary threaded plug is inserted from the outer convex side of the shell component prior to implantation of the shell component, thereby also reducing surgical flexibility. The use of the complimentary threaded plug may also not provide an effective seal, via the complimentary threads. The cement spacers are also merely used to provide for a uniform cement mantel and do not seal the holes in the shell component because of a bore passing through the cement spacers. Finally, removal of the closure members by an instrument in either of the above-identified devices may create scratches or scars on the inner concave surface of the shell component that will generally require a new shell component to be implanted.

What is needed then is an apparatus and method for plugging holes in an acetabular shell component which does not suffer from the above-mentioned disadvantages. This in turn, will provide more surgical flexibility during implantation of the acetabular prosthesis; reduce the potential for wear debris exiting the acetabular shell component; provide pre-installed plugs that may be removed once the acetabular shell component has been implanted; provide instrumentation to remove the plugs after implantation without the possibility of scratching the inner concave surface of the acetabular shell component; provide a more fluid tight seal; and reduce surgical time, cost and complexity. It is, therefore, an object of the present invention to provide such an apparatus and method for plugging holes in an acetabular shell component.

SUMMARY OF THE INVENTION

In accordance with the teachings of the present invention, an apparatus and method for plugging holes in an acetabular shell component is disclosed. The apparatus for plugging the holes is adapted to minimize migration of debris through the holes. In addition, the apparatus is further adapted to be removed after the acetabular shell component has been implanted without scratching the inner surface of the acetabular shell component using a removal instrument.

In one preferred embodiment, an acetabular prosthesis has at least one selectively pluggable hole and includes an acetabular shell component. The acetabular shell component has an inner concave surface and an outer convex surface with at least a first selectively pluggable hole passing therethrough. The first selectively pluggable hole is defined by at least a cylindrical threaded sidewall. The apparatus further includes a plug having a tapered threaded sidewall. The first selectively pluggable hole defined by the cylindrical threaded sidewall is operable to threadably receive the tapered threaded sidewall of the plug to create an interference fit which substantially seals the first selectively pluggable hole to minimize migration of debris through the first selectively pluggable hole.

In another preferred embodiment, an acetabular prosthesis has at least one selectively pluggable hole and includes an acetabular shell component. The acetabular shell component includes an inner concave surface and an outer convex surface with at least a first selectively pluggable hole passing therethrough. The first selectively pluggable hole is defined by at least a first sidewall. The apparatus further includes a plug having a second sidewall which engages the first sidewall of the first selectively pluggable hole to substantially seal the first selectively pluggable hole. A removal instrument is operable to removably engage the plug. The removal instrument includes means for preventing the inner concave surface of the acetabular shell component from being scratched during removal of the plug from the acetabular shell component.

Use of the present invention provides an apparatus and method for plugging holes in an acetabular shell component. As a result, the aforementioned disadvantages associated with the currently available techniques have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENT(S)

The following description of the preferred embodiments concerning an apparatus and method for plugging screw holes in an acetabular shell component are merely exemplary in nature and are not intended to limit the invention or its application or uses. Moreover, while the present invention is described in detail below with reference to performing implantation of a specific acetabular prosthesis, it will be appreciated by those skilled in the art that the present invention is clearly not limited to such an acetabular prosthesis and may be used with various other acetabular prostheses.

Figure 1:
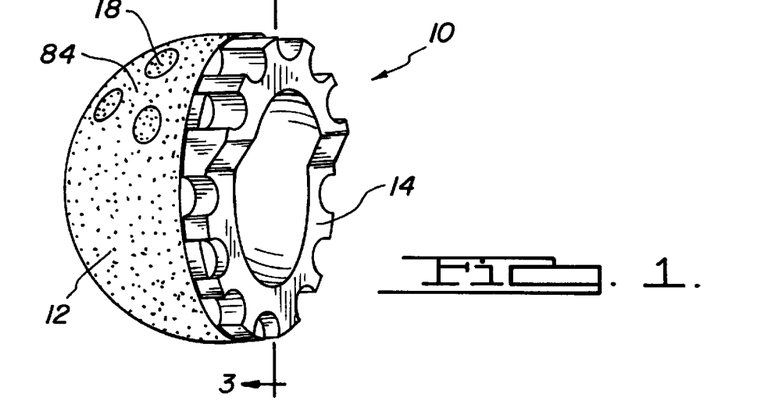
FIG. 1 is a perspective view of an assembled acetabular prosthesis according to the teachings of the preferred embodiment of the present invention.
Figure 2:
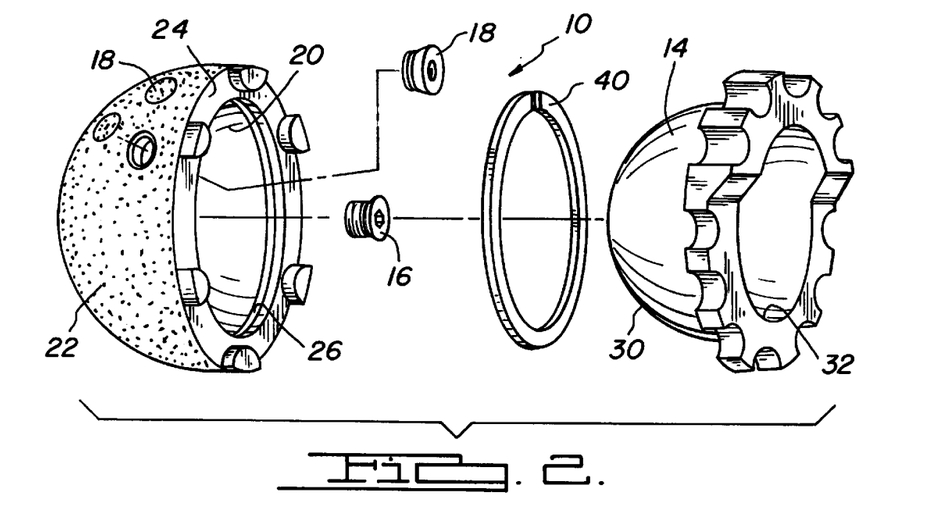
FIG. 2 is an exploded perspective view of the acetabular prosthesis of FIG. 1.
Figure 3:
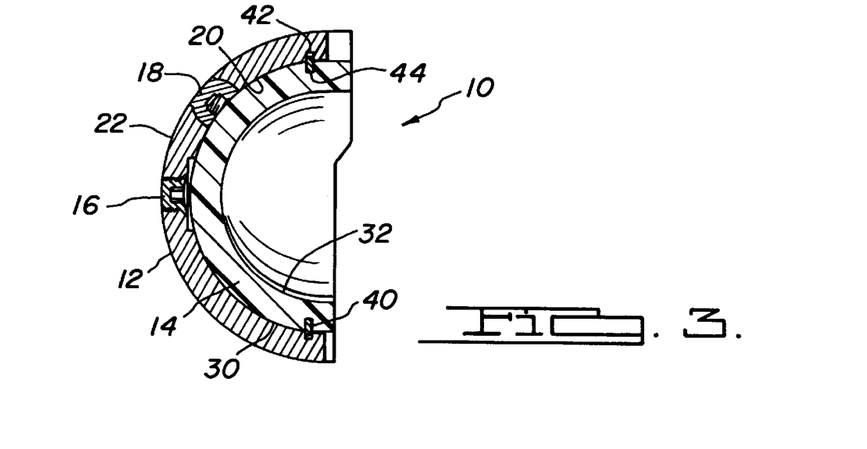
FIG. 3 is a side cross-sectional view taken along line 3—3 of FIG. 1.

Referring to FIGS. 1–3, an acetabular prosthesis 10 according to the teachings of a first preferred embodiment of the present invention is shown. The acetabular prosthesis 10 includes a full-hemisphere acetabular shell component 12, a congruent shell liner 14, an apical plug 16, and a plurality of pre-installed dome plugs 18. The acetabular shell component 12 includes a smooth inner concave surface 20 and a roughened or porous coated outer convex or medial surface 22. The acetabular shell component 12 is made from suitable biocompatible material such as titanium, stainless steel, titanium alloys, cobalt-chrome-molybdenum alloy and is preferably made of the titanium alloy TI-6AL-4V. The acetabular shell component 12 further includes an annular face 24 having a shoulder 26.

The shell liner 14 is preferably formed from polyethylene or other suitable liner material. The shell liner 14 includes an outer convex surface 30 and an inner concave surface 32. The outer convex surface 30 is fully congruent and mates with the inner concave surface 20 of the shell component 12 to minimize relative motion between the components. The inner concave surface 32 creates a uniform thickness of the shell liner 14 and acts as a bearing surface for a head of a hip prosthesis so as to dissipate stresses over the entire shell liner 14. The shell liner 14 is secured to the acetabular shell component 12 by means of a locking ring 40 that engages grooves 42 and 44 formed, respectively, into the shell component 12 and the shell liner 14. The locking ring 40 substantially reduces or eliminates micro-motion between the shell component 12 and the shell liner 14.

Figure 4:
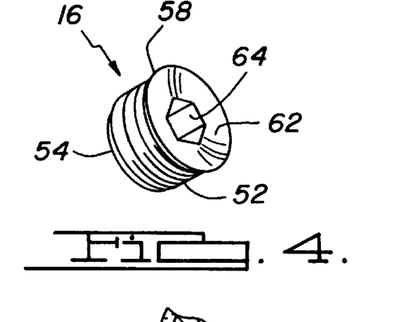
FIG. 4 is a perspective view of a threaded apical plug according to the teachings of the preferred embodiment of the present invention.
Figure 5:
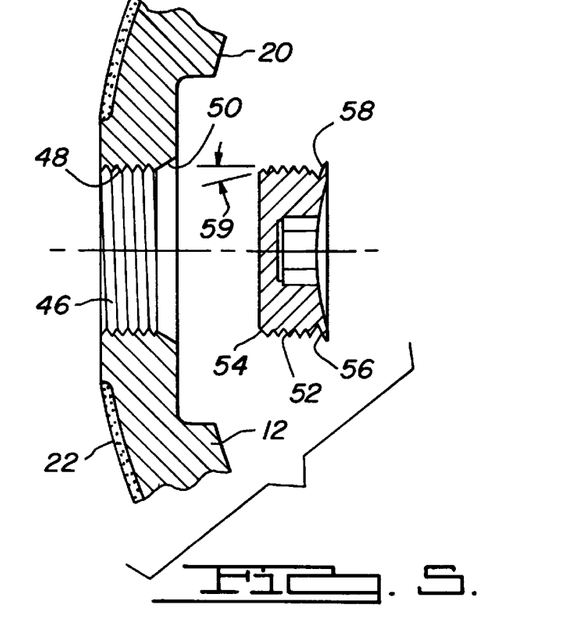
FIG. 5 is a side cross-sectional view of the threaded apical plug and threaded apical hole.
Figure 6:
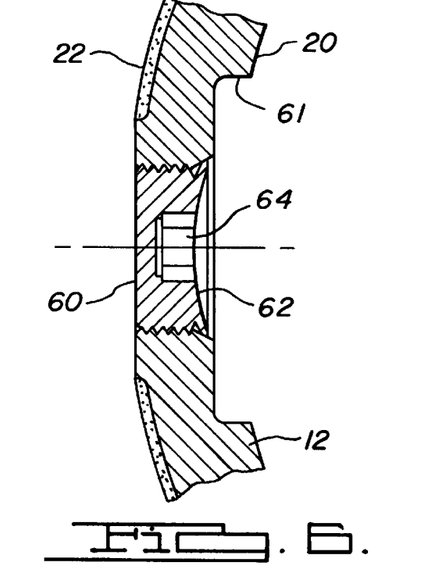
FIG. 6 is a side cross-sectional view of the threaded apical plug threaded into the threaded apical hole.

Referring to FIGS. 4–6, the threaded center or apical plug 16 which is preferably formed from the same titanium alloy as the acetabular shell component 12, is shown in operative association with a selectively pluggable threaded center or apical hole 46. The threaded apical hole 46 is defined by a cylindrical threaded sidewall 48 and a beveled shelf 50. The threaded apical hole 46 is used to receive various instruments, such as a threaded inserter, for use in implantation of the acetabular shell component 12, as well as for receiving the threaded apical plug 16.

The threaded apical plug 16 includes a conical or tapered threaded sidewall 52 having a chamfered end 54, a V-shaped groove 56 and a beveled seat 58. The tapered threaded sidewall 52 tapers at an angle 59 of about 4° to create an interference fit within the acetabular shell component 12 upon threading the apical plug 16 into the cylindrical threaded apical hole 46. The tapered threaded sidewall 52 threadably engages the cylindrical threaded sidewall 48, while the beveled seat 58 substantially seats against the beveled shelf 50, shown clearly in FIG. 6. The interference fit of the tapered threaded sidewall 52 with the cylindrical threaded sidewall 48, along with the beveled seat 58 engaging and mating with the beveled shelf 50 provides for a substantially fluid tight seal, thereby minimizing the migration of wear debris out of the shell component 12. The apical plug 16 further includes a planar exterior surface 60 and a spherical internal surface 62 having a hexagonal bore 64. The hexagonal bore 64 is engaged by a hex driver to install the apical plug 16 into the threaded apical hole 46. The spherical internal surface 62 accommodates for the shell liner 14.

Figure 7:
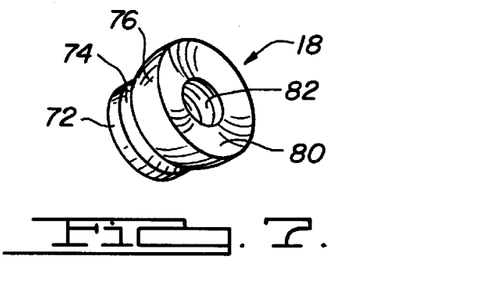
FIG. 7 is a perspective view of a dome plug according to the teachings of the preferred embodiment of the present invention.
Figure 8:
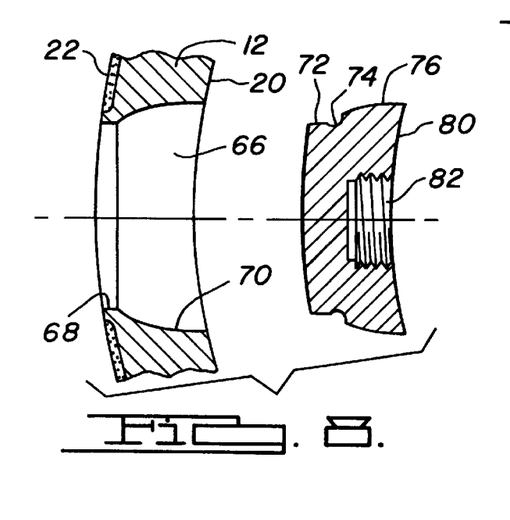
FIG. 8 is a side cross-sectional view of the dome plug and dome plug hole.
Figure 9:
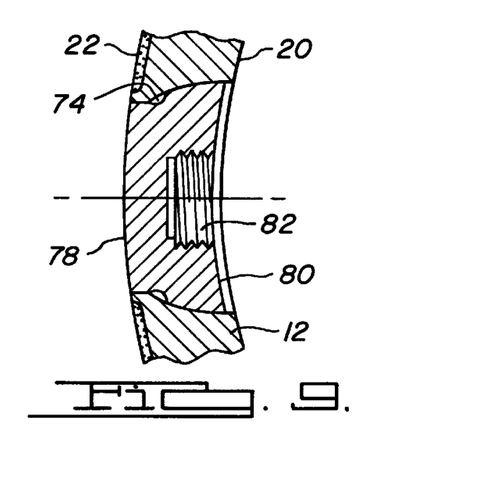
FIG. 9 is a side cross-sectional view of the dome plug engaged in the dome plug hole.

Referring to FIGS. 7–9, the dome plug 18, which is also preferably formed from the same titanium alloy as the acetabular shell component 12, is shown in operative association with a selectively pluggable dome hole 66. The dome hole 66 is defined by a cylindrical sidewall 68 and a spherical sidewall 70. The dome plug 18 includes a cylindrical sidewall 72, an arcuate groove 74 and a congruent spherical sidewall 76. The diameter of the cylindrical sidewall 72 of the dome plug 18 is larger than the diameter of the cylindrical sidewall 68 of the acetabular shell component 12 such that the dome plug 18 is press fit and matingly received into the dome hole 66 to substantially seal the dome hole 66 with the dome plug 18. For example, the cylindrical sidewall 68 of the dome hole 66 preferably has a diameter of about 0.2710 inches and the cylindrical sidewall 72 of the dome plug 18 preferably has a diameter of about 0.2719 inches.

Upon sealably engaging the sidewalls 68 and 72, the arcuate groove 74 allows the dome plug 18 to sit deeper within the dome hole 66 by providing relief in the dome plug 18 and eliminating a corner to allow full seating. The spherical sidewall 76 of the dome plug 18 also mates with the spherical sidewall 70 of the dome hole 66. The dome plug 18 further includes a spherical roughened or porous coated exterior surface 78 and a smooth spherical interior surface 80 having a threaded bore 82. The threaded bore 82 provides means for threadably receiving an instrument for removal of the dome plug 18. The exterior surface 78 is substantially flush with the porous coated surface 22 and the interior surface 80 seats slightly beneath or substantially flush with the inner concave surface 20.

The dome plugs 18 are positioned at a superior quadrant 84 of the acetabular shell component 12. Specifically, five pre-plugged dome holes 66 are in the superior quadrant 84 which receive five (5) press fit dome plugs 18. The dome plugs 18 are pre-installed into the acetabular shell component 12 by press fitting to provide a substantially fluid tight seal that will reduce the migration of debris to the medial convex side 22 of the shell component 12. If screw fixation is required, the desired dome plug 18 can be removed either before or after the acetabular shell component 12 is implanted into an acetabulum.

Figure 10:
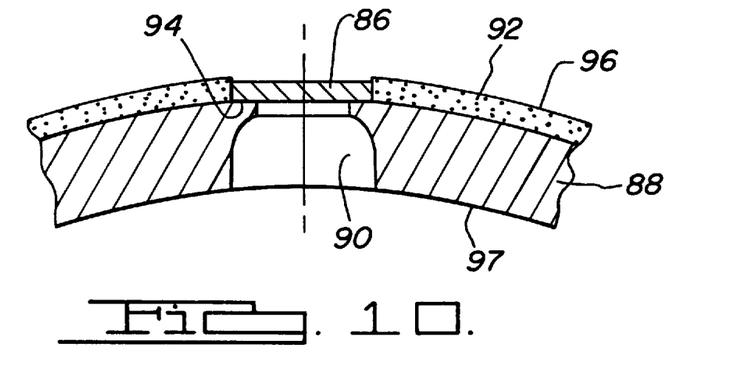
FIG. 10 is a side cross-sectional view of a plug according to the teachings of a second preferred embodiment of the present invention.

Referring to FIG. 10, a side cross-sectional view of a disk-shaped plug 86 according to the teachings of a second preferred embodiment of the present invention is shown. The plug 86 is preferably constructed from polymethylmethacrylate (PMMA) or other suitable biocompatible material and may be installed and fitted with various acetabular shell components 88 having holes 90. In other words, the plug 86 may be retrofitted to conventional acetabular shell components 88, custom acetabular shell components or revision-type acetabular shell components that do not have holes designed to receive specific shaped plugs, such as the apical plug 16 or the dome plugs 18. Since most acetabular shell components 88 include a porous coated surface 92, a ledge 94 is generally formed around the periphery of the hole 90. The plug 86 is secured to the ledge 94 by means of ultra-sonic energy, heat energy, mechanical or chemical bonding, or other appropriate fixation means. By use of non-mechanical fixation (i.e., chemical, etc.), a complete seal is achieved, which is sometimes very difficult to achieve with mechanical fixation.

Should it be required to utilize a fixation screw through the hole 90, the plug 86 may simply be removed by pushing through the hole 90 with an instrument, thereby knocking the plug 86 off the ledge 94, prior to implanting the acetabular shell component 88. Alternatively, the plug 86 may simply be drilled through prior to implantation of the acetabular shell component 88. Since the plug 86 is affixed to the outer convex surface 96 of the acetabular shell component 88, the plug 86 may be affixed to various acetabular shell components either before or during surgery should it be desirable to seal specific holes 90, thereby minimizing or restricting the flow of debris out through the medial convex side 96 of the acetabular shell component 88. Moreover, the plug 86 may also be used to keep cement out of the interior 97 of the acetabular shell component 88 should the acetabular shell component 88 be cemented in place.

In this way, the surgeon will have the option to use only screw fixation or cement fixation of the acetabular shell component 88, or a combination of both, providing further versatility. In addition, with biocompatible material used for the plug 86, in press-fit applications, the plug 86 may either be drilled through after press-fitting the acetabular shell component 88 or a self tapping fixation screw can simply be driven through the plug 86, providing a further seal around the fixation screw. Still further, should cement be used in combination with the fixation screws, here again, the plug 86 may be drilled through after cementing or a self-tapping fixation screw can simply be driven through the plug 86. This inhibits cement from entering the interior 97 of the acetabular shell component 88 and eliminates cement under the screw head.

Another important feature of the plug 86 is that PMMA is generally a transparent material and the plug 86 therefore acts as a "window" for the surgeon. This enables the surgeon to determine if proper seating of the acetabular shell component 88 is made, without having to have exposed holes 90. In addition, any other suitable transparent biocompatible material may also be used to provide similar results.

Figure 11A:
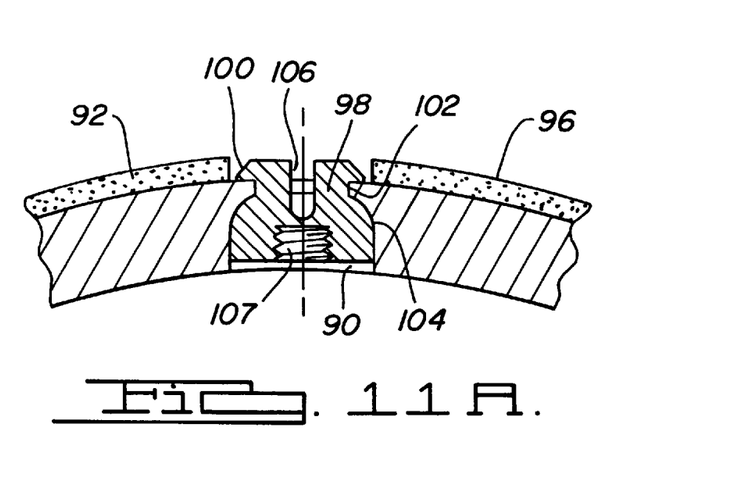
FIG. 11A is a side cross-sectional view of a plug according to the teachings of a third preferred embodiment of the present invention.
Figure 11B:
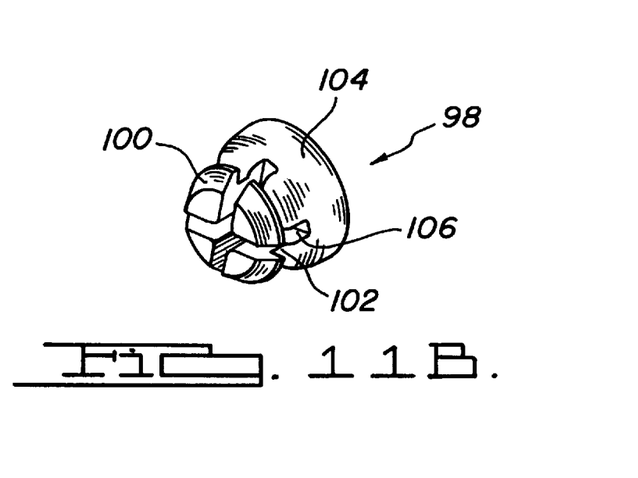
FIG. 11B is a perspective view of the plug shown in FIG. 11A.

Referring to FIGS. 11A–11B, a third preferred embodiment of a plug 98 is shown. The plug 98 is preferably constructed of the same titanium alloy as the acetabular shell component 12 and is made to snap into the hole 90 of the acetabular shell component 88. The plug 98 includes a tapered sidewall 100, a channel 102 and a spherical sidewall 104. The plug 98 further includes grooves 106 formed into the plug 98 which enables the plug 98 to flex as the plug 98 is snapped into the hole 90. A threaded bore 107 is also formed into the plug 98 to allow for removal of the plug 98, similar to the dome plugs 18. The plug 98 may be snapped into selected holes 90 either before or after implantation of the acetabular shell component 88. Here again, the plug 98 seals off the hole 90 in the acetabular shell component 88 to reduce or prevent wear debris from the acetabular shell component 88 and the shell liner 14 from passing through to the medial convex side 96 of acetabular shell component 88.

Figure 12:
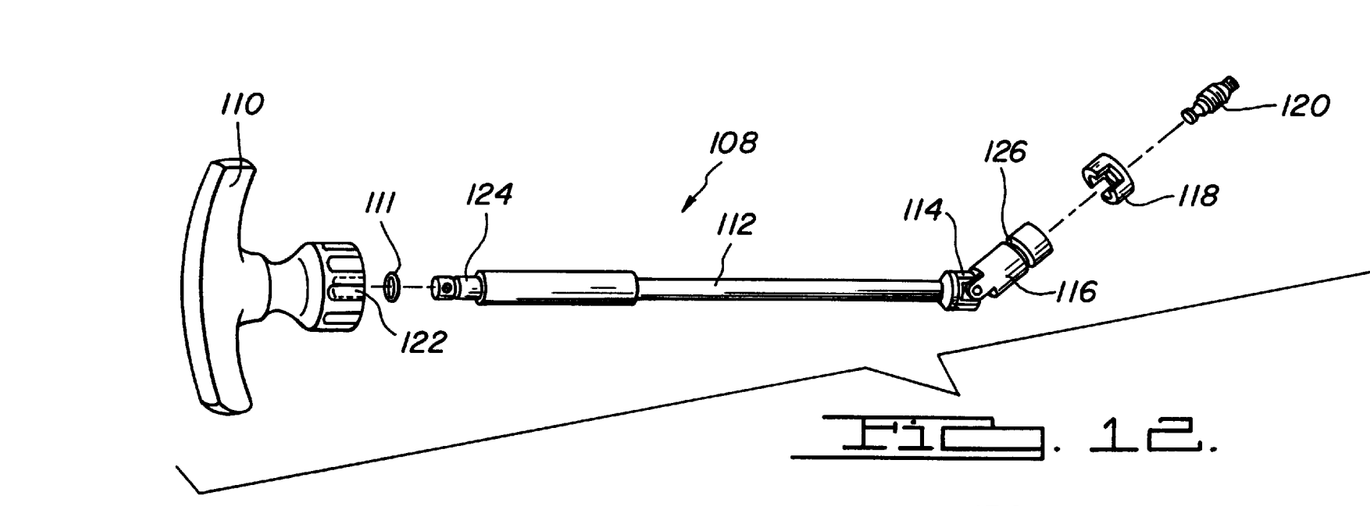
FIG. 12 is an exploded perspective view of a removal instrument utilized to remove the dome plug shown in FIG. 7.
Figure 13:
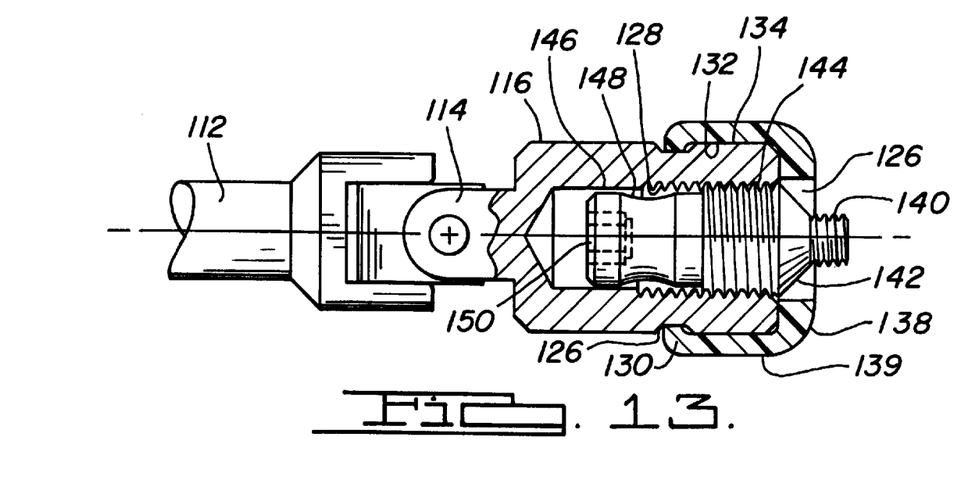
FIG. 13 is an assembled side cross-sectional view of one end of the removed instrument shown in FIG. 12.
Figure 14A:
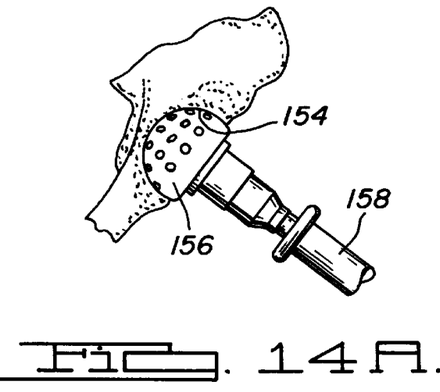
FIGS. 14A–14I illustrate a method for implanting the acetabular prosthesis according to the teachings of the preferred embodiment of the present invention.
Figure 14B:
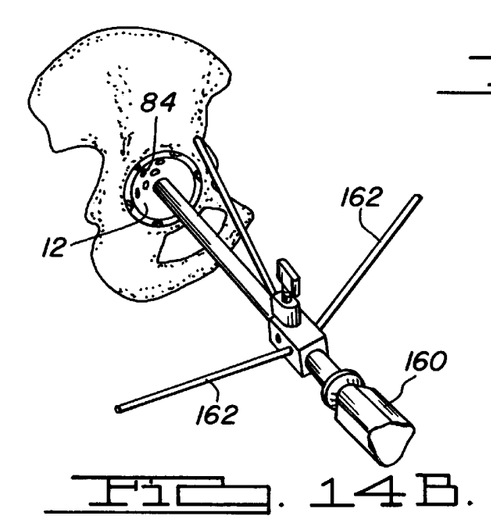
Figure 14C:
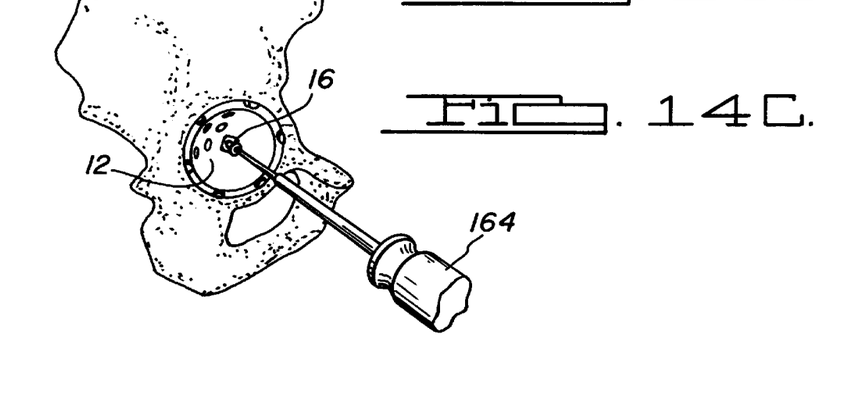
Figure 14D:
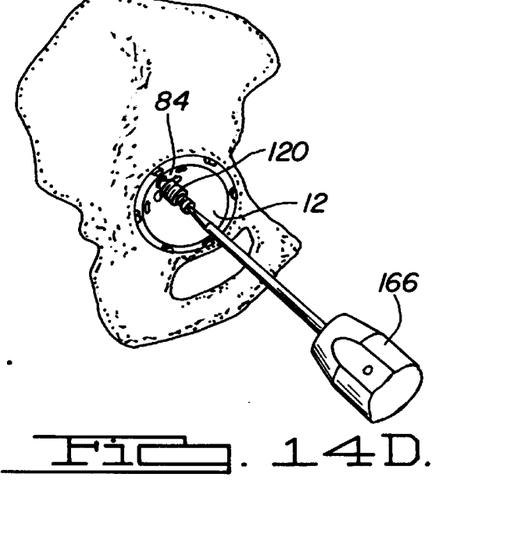
Figure 14E:
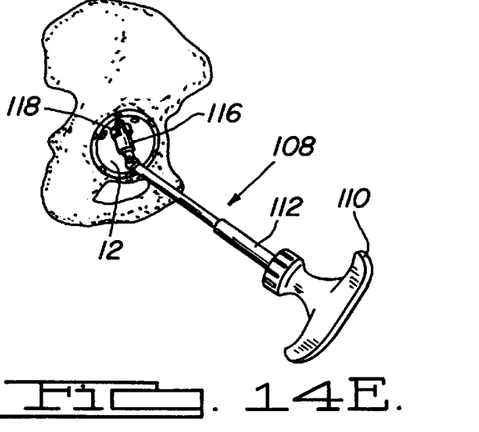
Figure 14F:
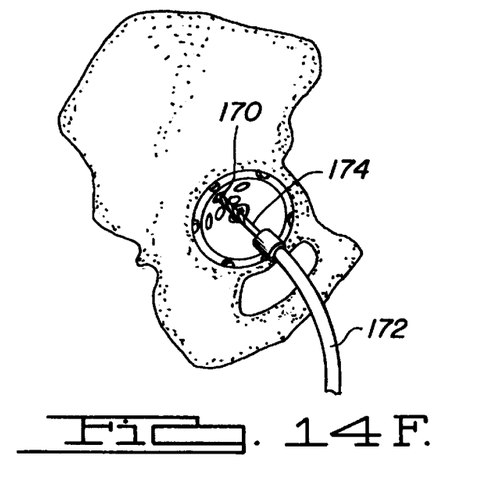
Figure 14G:
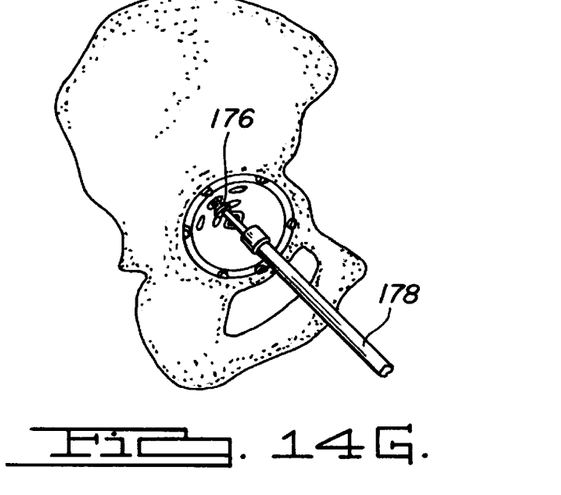
Figure 14H:
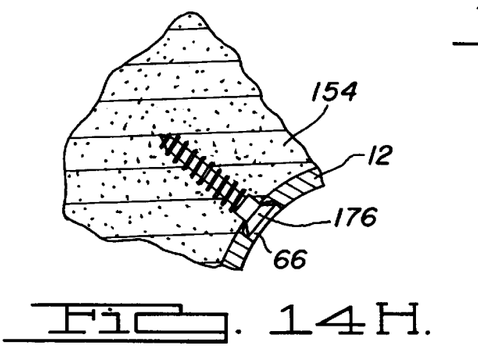
Figure 14I:
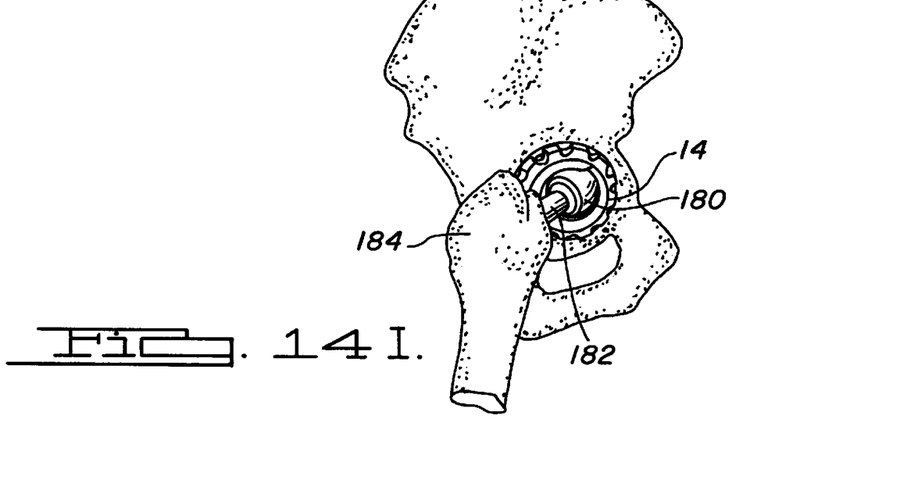

Turning now to FIGS. 12–13, a removal instrument 108 is utilized to remove the dome plug 18 according to the teachings of the preferred embodiment of the present invention is shown. The removal instrument 108 includes a ratchet handle 110, an O-ring 111, a rigid shaft 112 having a universal joint 114 and an internally threaded socket 116, a socket bearing or bushing 118 and a threaded plug puller knob 120. The ratchet handle 110 includes an internal ratchet mechanism and a bore 122 operable to receive a first end 124 of the rigid shaft 112 along with the O-ring 111. At the opposite end of the shaft 112 is the universal or swivel joint 114 and the socket 116. The socket 116 includes an external groove 126 and an internally threaded bore 128. The socket bushing 118 is preferably comprised of polyethylene and includes resilient fingers 130 which engage and resiliently snap into groove 126 such that an inner sidewall 132 of the bushing 118 mates with an outer sidewall 134 of the socket 116. The socket bushing 118 further includes a bore 126, an abutting face 138 and an outer cylindrical sidewall 139. The bore 126 is operable to pass the plug puller knob 120. The abutting face 138 and the outer cylindrical sidewall 139 provides a means for preventing the inner concave surface 20 from being scratched or scarred by the removal instrument 108 during removal of a dome plug 18. The abutting face 138 may be convex to better mate with the inner concave surface 20. The abutting face 138 further acts as a bushing face to reduce friction as the bushing 118 engages the inner concave surface 20.

The plug puller knob 120 includes a threaded finger 140, a tapered sidewall 142, a cylindrical threaded sidewall 144, and a cylindrical neck portion 146 having a tapered region 148. The neck 146 further includes a hexagonal bore 150 operable to receive a hex driver. The threaded finger 140 threadably engages the threaded bore 82 of the dome plug 18. The threaded sidewall 144 is threadably received by the internal threaded sidewall 128 of socket 116.

The removal instrument 108 is assembled by connecting the ratchet handle 110 to the shaft 112, via the bore 122. The socket bushing 118 is snapped around the outer cylindrical sidewall 134 of the socket 116, as the fingers 130 engage the groove 126. The socket bushing 118 prevents the removal instrument 108 from scratching or scarring the inner concave surface 20 of the acetabular shell component 12 upon removal of the selected dome plug 18. The plug puller knob 120 is threadably received within the socket 116, via the internal threaded sidewall 128 and the threaded sidewall 144.

The method for implanting the acetabular prosthesis 10, including the method for plugging/unplugging the holes in the acetabular shell component 12 will now be described with reference to FIGS. 14A–14I. Once a radiograph or x-ray has been taken of the hip that is to be replaced, a suitably sized acetabular prosthesis 10 is selected which may involve the use of a suitably sized template, as is well known in the art. Once the suitably sized acetabular prosthesis 10 is chosen, a suitably sized hip prosthesis is chosen to fit within the intramedullary canal of a host femur. The hip prosthesis may include many different types of hip prosthesis such as the Bi-Metric System, Mallory/Head System or Integral System, each available from Biomet Inc. After the suitably sized acetabular prosthesis 10 and hip prosthesis are selected, the femur is dislocated to expose the acetabulum 154. The hip prosthesis is then implanted in a manner well known in the art.

Once the hip prosthesis has been implanted, the acetabulum 154 is reamed with a reamer 156 driven by a driver 158. The acetabulum 154 is generally hemispherically reamed until concentric removal of all acetabular cartilage is achieved. Once the acetabulum 154 has been appropriately reamed, acetabular trial gauges, which are well known in the art, may be used to determine or confirm the diameter of the acetabular shell component 12 to be used. With the proper sized acetabular shell component 12 selected, an impacting or inserting instrument 160 is threaded into the threaded hole 46 of the acetabular shell component 12. The inserting instrument 160 comes to rest at a rectangular depression 161 in the shell component 12 and is used to properly position the acetabular shell component 12 by use of guide rods 162. It should further be noted that placement of fixation screws is generally in the superior posterior quadrant 84 should screw fixation be required.

Once the orientation of the acetabular shell component 12 is acceptable, the inserter 160 is solidly impacted to fully seat the acetabular shell component 12, such that firm rim fixation is achieved. Once the acetabular shell component 12 has been solidly impacted and affixed, the inserter 160 is then carefully removed from the threaded hole 46, thereby threadably disengaging the inserter 160 from the acetabular shell component 12.

After stability has been assessed, the apical hole 46 is sealed with the apical plug 16. The hexagonal bore 64 of the apical plug 16 is engaged by a 2.5 millimeter hex screwdriver 164 that is used to tighten the apical plug 16 into the acetabular shell component 12. As the tapered apical plug 16 is threaded into the cylindrical threaded hole 46, the tapered threaded sidewall 52 threadably engages the cylindrical threaded sidewall 48 and the beveled seat 58 engages the beveled shelf 50, thereby providing a substantially fluid tight seal between the inner concave surface 20 and the medial outer convex surface 22.

If after implantation of the acetabular shell component 12 or prior to implantation, it is determined that fixation screws are needed for additional fixation, selected dome plugs 18 can be removed using the removal instrument 108. The five dome plugs 18 are positioned in a clustered arrangement in the superior posterior quadrant 84 in one embodiment to allow for fixation in several areas within this quadrant 84. However, the dome plugs 18 may be positioned in any location about the acetabular shell component 12. Once it is determined which dome plugs 18 should be removed, the plug puller knob 120 having threaded finger 140 is threaded into the threaded bore 82 of the selected dome plug 18 using a 3.5 millimeter hex driver 166 which engages the hexagonal bore 150 of the plug puller knob 120. Once the plug puller knob 120 is fully threaded and seated in the selected dome plug 18, the polyethylene bushing 118 and socket 116 of the removal instrument 108 are placed over the plug puller knob 120.

Upon turning the removal tool 108 in a clockwise turning motion, the socket 116 having internal threaded sidewall 128, threadably receives the plug puller knob 120, via the threaded sidewall 144. The abutting face 138 of the bushing 118, as well as the outer sidewall 139 of the bushing 118 prevents the smooth inner concave surface 20 from being scratched or scarred during removal of the selected dome plug 18. With the socket 116 fully engaging the plug puller knob 120, the abutting face 138 engages the inner concave surface 20. The removal instrument 108 is then further rotated clockwise, via the ratchet handle 110. This additional turning draws the plug puller knob 120 further up into the threaded socket 116 to break the press fit seal and easily remove the selected dome plug 18.

Once again, the selected dome plug 18 may either be removed before or after the acetabular shell component 12 has been implanted into the acetabulum 154. Removal of the dome plug 18 after implantation of the shell component 12 is achieved since the removal instrument 108 does not create an axial or transverse pulling force on the shell component 12. In other words, the shell component 12 is held firmly in place as it is being engaged by the bushing 118, and the dome plug 18 seal is broken by both rotational and axially forces being applied to the dome plug 18 during the drawing up of the plug puller knob 120 into the socket 116.

After threadably removing the dome plug 18 from the plug puller knob 120 and once all of the selected dome plugs 18 have been removed as described above, the bushing 118 and the plug puller knob 120 may be disposed of. The fixation screw holes 170 are then drilled into the acetabulum 154 using a flexible drill shaft 172 and a drill bit 174. An optional drill guide, as known in the art, may be used to position the drill bit 174 relative to the hole 66. Once the fixation holes 170 have been drilled, a depth gauge, as is also known in the art, may be used to determine the length of the screw. With the length of the screw determined, a fixation screw 176 is inserted into the screw hole 170 using a universal screw driver 178. With the fixation screws 176 firmly secured and seated in the dome holes 66, the acetabular shell component 12 may be thoroughly cleaned and a trial liner, as known in the art, may be inserted into the acetabular shell component 12.

With the trial liner inserted, a trial reduction can be carried out to check the full range of motion including extension, external rotation, flexion, and abduction. After trial reduction, the shell liner 14 is firmly seated within the acetabular shell component 12. The shell liner 14 is appropriately seated by firmly impacting the shell liner 14 against the acetabular shell component 12. With the shell liner 14 fully seated, the ring-lock 40 engages the grooves 42 and 44, thereby preventing movement of the shell liner 14 relative to the acetabular shell component 12. A head 180 of a hip prosthesis 182 which is implanted into a femur 184 is then installed in a manner known in the art into the acetabular prosthesis 10 with the head 180 bearing on the shell liner 14.

Use of both the apical plug 16 and the dome plugs 18 substantially reduces or eliminates any wear debris occurring within the inner concave surface 12 from migrating through the acetabular shell component 12 to the outer convex surface 22. In addition, use of the apical plug 16 and the dome plugs 18 further enables a cement mantle to be formed along the outer convex surface 22, should it be desired, without having cement enter the inner concave surface 20. Moreover, by providing pre-installed dome plugs 18 which may be removed either before or after implantation of the acetabular shell component 12, surgical time is reduced, as well as surgical flexibility increased, thereby lowering overall surgical cost.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. An acetabular prosthesis having at least one selectively pluggable hole, said acetabular prosthesis comprising:

an acetabular shell component having an inner concave surface and an outer convex surface with at least a first selectively pluggable hole passing therethrough, said first selectively pluggable hole defined by at least a first sidewall;

a plug having a second sidewall, said second sidewall of said plug operable to engage said first sidewall of said first selectively pluggable hole to substantially seal said first selectively pluggable hole; and a removal instrument operable to removably engage said plug, said removal instrument including a means for preventing said inner concave surface of said acetabular shell component from being scratched during removal of said plug from said acetabular shell component with said removal instrument.

2. The acetabular prosthesis as defined in claim 1 wherein said plug further includes a threaded bore and said removal instrument further includes a threaded finger operable to threadably engage said threaded bore.

3. The acetabular prosthesis as defined in claim 1 wherein said removal instrument further includes a plug puller knob having a first threaded sidewall and a second threaded sidewall and a socket having an internal threaded bore, said first threaded sidewall of said plug puller knob operable to threadably engage a threaded bore in said plug and said second threaded sidewall of said plug puller knob operable to be threadably received by said internal threaded bore of said socket, whereby upon rotating said socket draws said plug puller knob into said internal threaded bore to rotate and remove said plug from said acetabular shell component.

4. The acetabular prosthesis as defined in claim 3 wherein said means for preventing said inner concave surface of said acetabular shell component from being scratched includes a polymeric bushing operable to mate with an outer sidewall of said socket.

5. The acetabular prosthesis as defined in claim 4 wherein said bushing includes at least one resilient finger which engages and resiliently snaps into a groove formed into said outer sidewall of said socket and an abutting face and an outer cylindrical sidewall which prevents said inner concave surface of said acetabular shell component from being scratched during removal of said plug by said removal instrument.

6. The acetabular prosthesis as defined in claim 1 wherein said removal instrument is operable to removably engage said plug after said acetabular shell component has been implanted into an acetabulum.

7. The acetabular prosthesis as defined in claim 1 wherein said acetabular prosthesis further includes an apical plug having a tapered threaded sidewall, and said acetabular shell component further includes a second selectively pluggable hole defined by a cylindrical threaded sidewall, whereby said tapered threaded sidewall of said apical plug forms an interference fit with said cylindrical threaded sidewall of said second selectively pluggable hole.

8. An acetabular prosthesis having at least one selectively pluggable hole, said acetabular prosthesis comprising:

an acetabular shell component having an inner concave surface and an outer convex surface with at least a first selectively pluggable hole passing therethrough, said first selectively pluggable hole defined by at least a first sidewall;

a plug having a second sidewall and a threaded bore, said second sidewall of said plug operable to engage said first sidewall of said first selectively pluggable hole to substantially seal said first selectively pluggable hole; and a removal instrument operable to remove said plug from said first selectively pluggable hole, said removal instrument including:

a plug puller knob having a first threaded sidewall and a second threaded sidewall, said first threaded sidewall operable to threadably engage said threaded bore of said plug, and a socket having an internal threaded bore, said internal threaded bore operable to threadably receive said second threaded sidewall of said plug puller knob, wherein rotating said socket draws said plug puller knob into said internal threaded bore to rotate and remove said plug from said acetabular shell component.

9. The acetabular prosthesis as defined in claim 8 wherein said acetabular prosthesis further includes an apical plug having a tapered threaded sidewall, and said acetabular shell component further includes a second selectively pluggable hole defined by a cylindrical threaded sidewall, whereby said tapered threaded sidewall of said apical plug forms an interference fit with said cylindrical threaded sidewall of said second selectively pluggable hole.

10. The acetabular prosthesis as defined in claim 8 wherein said removable instrument further includes a polymeric bushing having an abutting face and an outer cylindrical sidewall which are operable to prevent the inner concave surface of said acetabular shell component from being scratched by said removal instrument during removal of said plug.

11. The acetabular prosthesis as defined in claim 10 wherein said abutting face of said polymeric bushing engages said inner concave surface of said acetabular shell component upon rotating said socket, whereby said acetabular shell component is firmly engaged by said bushing so as not to create an axial pulling force on said acetabular shell component during removal of said plug after said acetabular shell component has been implanted into an acetabulum.

* * * * *